United States Patent
Pavlovic et al.

(10) Patent No.: US 6,807,491 B2
(45) Date of Patent: Oct. 19, 2004

(54) METHOD AND APPARATUS FOR COMBINING GENE PREDICTIONS USING BAYESIAN NETWORKS

(75) Inventors: Vladimir Pavlovic, Melrose, MA (US); Simon Kasif, Newton, MA (US); Ashutosh Garg, Urbana, IL (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 324 days.

(21) Appl. No.: 09/943,579

(22) Filed: Aug. 30, 2001

(65) Prior Publication Data

US 2003/0077586 A1 Apr. 24, 2003

(51) Int. Cl.[7] ................................................. G06N 3/12
(52) U.S. Cl. ......................................... 702/20; 706/13
(58) Field of Search ............................... 702/20; 706/13

(56) References Cited

PUBLICATIONS

Burge, C. and S. Karlin, "Prediction of Complete Gene Structures in Human Genomic DNA," *J. Mol. Biol.* 266:78–94 (1997).
Salzberg, S. et al., "Microbial gene identification using interpolated Markov models," *Nucleic Acids Research*, 26(2) :544–548 (1998).
Xu, L. et al, "GRAIL: A Multi–Agent Neural Network System for Gene Identification," *Proc. IEEE* 84(10) :1544–1552 (1996).
Kulp, D. et al., "A Generalized Hidden Markov Model for the Recognition of Human Genes in DNA," in *ISMB–96: Proc. Fourth Intl. Conf. Intelligent Systems for Molecular Biology*, pp. 134–141, Menlo Park, CA, 1996; AAAI Press.

Borodovsky, M. and J. McInnich, "Genmark: Parallel Gene Recognition for Both DNA Strands," *Computers Chem.* 17(2):123–133 (1993).
Salzberg, S.L. et al. eds, *Computational Methods in Molecular Biology*, (Amsterdam: Elsevier) 1998; pp xv–xxiii.
Fraser, C.M. et al., Genomic sequence of a Lyme disease spirochaete, *Borrelia burgdorferi*, Nature 390: 580–586 Dec. 1997.
Murakami, K. and T. Takagi, "Gene recognition by combination of several gene–finding programs," *Bioinformatics* 14(8):665–675 (1998).
Salamov, A.A. and V.V. Solovyev, Ab initio Gene Finding in *Drosophila* Genomic DNA, *Genome Research* 10:516–522 (2000).
Reese, M.G. et al., Genie—Gene Finding in *Drosophila melanogaster*, *Genome Research* 10:529–538 (2000).
Krogh, A., Using Database Matches with HMM Gene for Automated Gene Detection in *Drosophila*, *Genome Research* 10:523–528 (2000).
Jordan, M.I. and R.A. Jacobs, Hierarchical Mixtures of Experts and the AM Algorithm, *Neural Computation* 6:181–214 (1994).
Wolpert, D.H., "Stacked Generalization," *Neural Networks* 5:241–259 (1992).
Cai, D. et al., "Modeling splice sites with Bayes networks," *Bioinformatics*, 16(2) :152–158 (2000).

*Primary Examiner*—Marjorie Moran

(57) ABSTRACT

Computer based apparatus and method automates gene prediction in a subject genomic sequence. A plurality of expert systems provide preliminary or intermediate gene predictions. A Bayesian network combiner combines the intermediate gene predictions and forms a final gene prediction. The final gene prediction accounts for dependencies between individual expert systems and dependencies between adjacent parts of the subject genomic sequence.

9 Claims, 3 Drawing Sheets

METHOD AND APPARATUS FOR COMBINING GENE PREDICTIONS USING BAYESIAN NETWORKS

BACKGROUND OF THE INVENTION

Most eukaryotic cells have an operational center called the nucleus which contains structures called chromosomes. Chemically, chromosomes are formed of deoxyribonucleic acid (DNA) and associated protein molecules. Each chromosome may have tens of thousands of genes. Some genes are referred to as "encoding" (or carrying information for constructing) proteins which are essential in the structuring, functioning and regulating of cells, tissues and organs. Thus, for each organism, the components of the DNA molecules encode much of the information necessary for creating and maintaining life of the organism. See Human Genome Program, U.S. Department of Energy, "Primer on Molecular Genetics", Washington, D.C., 1992.

The shape of a DNA molecule can be thought of as a twisted ladder. That is, the DNA molecule is formed of two parallel side strands of sugar and phosphate molecules connected by orthogonal/cross pieces (rungs) of nitrogen-containing chemicals called bases. Each long side strand is formed of a particular series of units called nucleotides. Each nucleotide comprises one sugar, one phosphate and a nitrogenous base. The order of the bases in this series (the side strands series of nucleotides) is called the DNA sequence.

Each rung forms a relatively weak bond between respective bases, one on each side strand. The term "base pairs" refers to the bases at opposite ends of a rung, with one base being on one side strand of the DNA molecule and the other base being on the second side strand of the DNA molecule. Genome size or sequence length is typically stated in terms of number of base pairs.

There are four different bases present in DNA: adenine (A), thymine (T), cytosine (C) and guanine (G). Adenine will pair only with thymine (an A-T pair) and cytosine will pair only with guanine (a C-G pair). A DNA sequence is represented in writing using A's, C's, T's and G's (respective abbreviations for the bases) in corresponding series or character strings. That is, the ACTG's are written in the order of the nucleotides of the subject DNA molecule.

As previously mentioned, each DNA molecule contains many genes. A gene is a specific sequence of nucleoticlo bases. These sequences carry the information required for constructing proteins. A protein is a large molecule formed of one or more chains of amino acids in a specific order. Order is determined by base sequence of nucleotides in the gene coding for the protein. Each protein has a unique function. In DNA molecule there are protein-coding sequences (genes) called "exons", and non-coding-function sequences called "introns" interspersed within many genes. The balance of DNA sequences in the genome are other non-coding regions or intergenic regions.

According to the foregoing method of representing genome and DNA sequences, the DNA sequence specifies the genetic instructions required to create a particular organism with its own unique traits and at the same time provides a text (character string) environment in which to study the same.

Biology and biotechnology are undergoing a technological revolution which is transforming research into an information-rich enterprise. Novel technologies such as high-throughput DNA sequencing and DNA microarrays are generating unprecedented amounts of data. A typical bacterial genome sequence is comprised of several million bases of DNA and contains several thousand genes. Many microbial genomes have been sequenced by the major genome centers, and the total number of such "small" genomes is expected to reach 100 shortly. Substantial progress is being made on sequencing the genomes of higher organisms as well. The genomes of eukaryotes are typically much larger; e.g., the human genome is approximately 3 billion bases long and is expected to contain approximately 100,000 genes.

Gene identification and gene discovery in newly sequenced genomic sequences is one of the most timely computational questions addressed by bioinformatics scientists. Popular gene finding systems include Glimmer, Geumark, Genscan, Genie, GENEWISE, and Grail (See Burge, C. and S. Karlin, "Prediction of complete gene structures in human genomic DNA," J Mol. Biol., 268:78–94, 1997; Salzberg, S. et al., "Microbial gene identification using interpolated Markov models," Nucl. Acids Res., 26(2):544–548, 1998; Xu, Y. at al., "Grail: A multi-agent neural network system for gene identification," Proc. of the IEEE, 84(10):1544–1552, 1996; Kulp, D. et al., "A generalized hidden Markov model for the recognition of human genes in DNA," in ISMB-96: Proc. Fourth Intl. Conf. Intelligent Systems for Molecular Biology, pp. 134–141. Menlo Park, Calif., 1996, AAAI Press; Borodovsky, M. and J. D. Mcininch, "Genemark: Parallel gene recognition for both DNA strands," Computers & Chemistry, 17(2):123–133, 1993; and Salzberg, S. et al. eds., Computational Methods in Molecular Biology, Vol. 32 of New Comprehensive Biochemistry, Elsevier Science B.V., Amsterdam, 1998). The annotations produced by gene finding systems have been made available to the public. Such projects include the genomes of over thirty microbial organisms, as well as Malaria, Drosophila, C.elegans, mouse, Human chromosome 22 and others. For instance. Glimmer has been widely used in the analysis of many microbial genomes and has reported over 98% accuracy in prediction accuracy (See Fraser, C. M. et al., "Genomic sequence of a Lyme disease spirochaete, Borrelia burgdorferi," Nature 390(6680):580–586, December 1997). Genie (D. Kulp et al. above) has been deployed in the analysis of the Drosophila genome, and Genscan (C. Burge and S. Karlin above) was used for analysis of human chromosome 22.

In addition to these central projects, a large number of proprietary genome analysis projects using gene-finding systems are in progress at the major bioinformatics centers in drug companies, bioinformatics companies, and other industrial organizations. As a result, a large number of research projects are underway in the goal of improving the performance of such systems, primarily targeting improvements in accuracy of reported genes. In fact, one of the current controversies involves producing an accurate estimate on the number of genes in the human genome. The current number of genes actually found by the gene finding programs are substantially lower than previous estimates.

Typically, the cellular machinery reads the bases on either strand of an input DNA sequence but in different directions depending on which strand it is reading. DNA is transcribed into RNA and then translated into proteins using a genetic code, which reads the bases in groups of 3 (called codons) and translates each codon into one amino acid. Amino acids are chained into molecules known as proteins. Levels of gene expression influence levels of protein expression which in turn influence the particular biological function it encodes.

On a very high level, genes in human DNA and many other organisms have a relatively simple structure. All eukaryotic genes, including human genes, are thought to share a similar layout. This layout adheres to the following "grammar" or pattern: start codon, exon, (intron-exon)$_n$, stop codon. The start codon is a specific 3-base sequence (e.g. ATG) which signals the beginning of the gene. Exons are the actual genetic material that code for proteins as mentioned above. Introns are the spacer segments of DNA whose function is not clearly understood. And finally stop codons (e.g TAA) which signal the end of the gene. The notation (intron-exon)$_n$, simply means that there are n alternating intron-exon segments. Genes identification procedures has to take into account other important issues such as polyA tail, promoters, pseudo-genes, alternative splicing and other features.

SUMMARY OF THE INVENTION

The proliferation of gene prediction systems, especially systems that focus on exon prediction raises the question whether a careful combination of the predictions made by these systems would produce a significantly improved gene detection system. The present invention systematically builds on the framework for a combination of experts.

General theory for the combination of experts has drawn significant interest in the machine learning community. Theory and practice of combining experts have been studied in literature. The choice of a particular way of combining expert predictions depends on the properties of individual experts and the demands posed by the problem at hand.

Most techniques for combining gene predictions proposed in the past have been rather trivial or have relied on ad hoc combinations of experts. In one prior project, Murakami and Takagi (Murakami, K. and T. Takagi, "Gene recognition by combination of several gene-finding programs," *Bioinformatics*, 14(8):665–675, 1998) proposed a system for gene recognition that combines several gene-finding programs. They implemented an AND and OR combination, HIGHEST-method (best individual expert), RULE-method (decisions using sets of expert rules), and an ad hoc BOUNDARY-method. The best of these methods achieved an improvement in general accuracy of 3%–5% over the individual gene finders.

Another similar expert combination scheme based on majority voting was recently used at The Institute for Genomic Research (TIGR) and reported in the 12th International Genome Sequencing Conference, September 2000. However, it only achieved moderate improvements in prediction.

In the present invention, apparatus and method for automated gene prediction operate as follows:

Using a plurality of expert systems (or similar units), gene locations in a subject genomic sequence are preliminarily predicted. Next, using a Bayesian network, the preliminarily predicted gene locations are combined to form a final combined output. The final combined output indicates predicted genes of the subject genomic sequence. The Bayesian network combiner accounts for dependencies between individual expert systems and dependencies between adjacent parts of the subject genomic sequence.

Preferably, the Bayesian network combines the preliminarily predicted gene locations according to $$Y_t^* = \max_{Y_t} P(Y|E_1 \ldots E_n, Y_{t-1}^*)$$

where t is location in the subject genomic sequence and $E_1, \ldots, E_n$ are the respective predicted gene locations of individual expert systems, n being the number of expert systems in the plurality.

In accordance with another aspect of the present invention, the preliminarily predicted gene locations and/or predicted genes include exon (or coding regions) predictions. Alternatively, the gene locations for predicted genes are indicated by exons and introns (i.e., coding and non-coding regions) of the subject genome sequence.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

By way of background, exons are the sequence regions that are translated into proteins by a simple but still computationally mysterious mechanism of splicing that takes place after the DNA sequence has been transcribed into RNA. The process starts by spliceome proteins that recognize the splice signals, followed by a step where the introns are cut out (spliced out), and ending in a phase where the consecutive exons are "glued" together into a single sequence that is translated into a protein. Intuitively speaking this process is performed on an RNA "image" of the genomic sequence.

During the translation, each codon is translated into a single amino acid, and the resulting sequence of amino acids produces a protein. There are 20 different amino acids, thus, a codon that consists of three bases provides sufficient information for creating a single amino acid.

The main problem facing automated methods for gene discovery is the fact that the current understanding of the genomic transcription process is not sufficient to produce a perfect predictive model of gene recognition in whole genomes. For instance, the "signals" for start coding (e.g, ATG) and end coding (e.g. TAA) are relatively short DNA sequences that appear very frequently in both coding and non-coding regions of DNA. Similarly, the regions where splicing occurs (splice sites) have relatively weak consensus (based on current data), and most consensus bases automated detection methods for splice detection have relatively high false positive rates.

Nevertheless, a number of successful gene finding systems have been built. Predictive gene finding systems focus on de novo gene discovery, namely predicting genes that have not been previously recorded. This process often uses probabilistic, statistical or other learning algorithms for training a set of models for known genes, and subsequently uses these models to predict new genes in the data. Such systems record very high level of accuracy when tested on isolated single gene regions but need improvement in the "real test" of gene finding in whole newly sequenced genomes.

The present invention is a system for the combination of individual experts which is learned from data. Unlike the prior art, such a system exploits learned dependencies between experts and forms a prediction maximally consistent with known gene data. Statistically, predictions of the invention system will then have the potential to generalize to genes undiscovered by any of the individual experts.

An attractive methology that exploits the joint statistics of expert systems and avoids the shortcomings of the prior art is based on Bayesian networks.

Figure 1A:
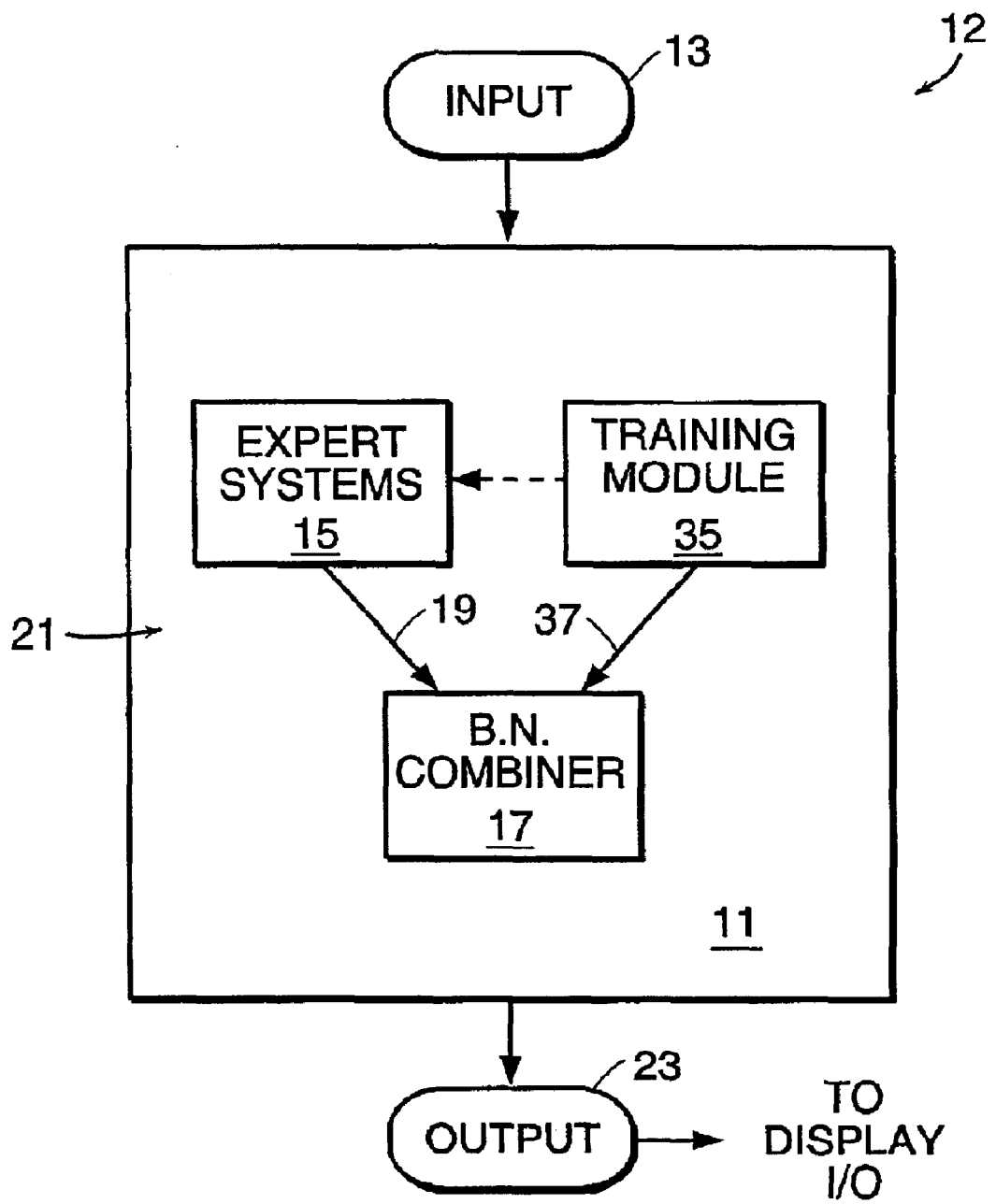
FIGS. 1A and 1B are schematic views of computer apparatus employing the present invention.

Illustrated in FIG. 1A is a computer apparatus 12 embodying the present invention. A digital processor 11 receives on input 13 a character string representing a subject nucleotide or genomic sequence. Input 13 is provided to digital processor 11 by another computer, another program, I/O accessories such as a keyboard, mouse or other cursor control/input means, and the like. In response to the input, digital processor 11 executes invention software 21 to determine exons/genes and hence proteins in the subject nucleotide sequence.

Figure 1B:
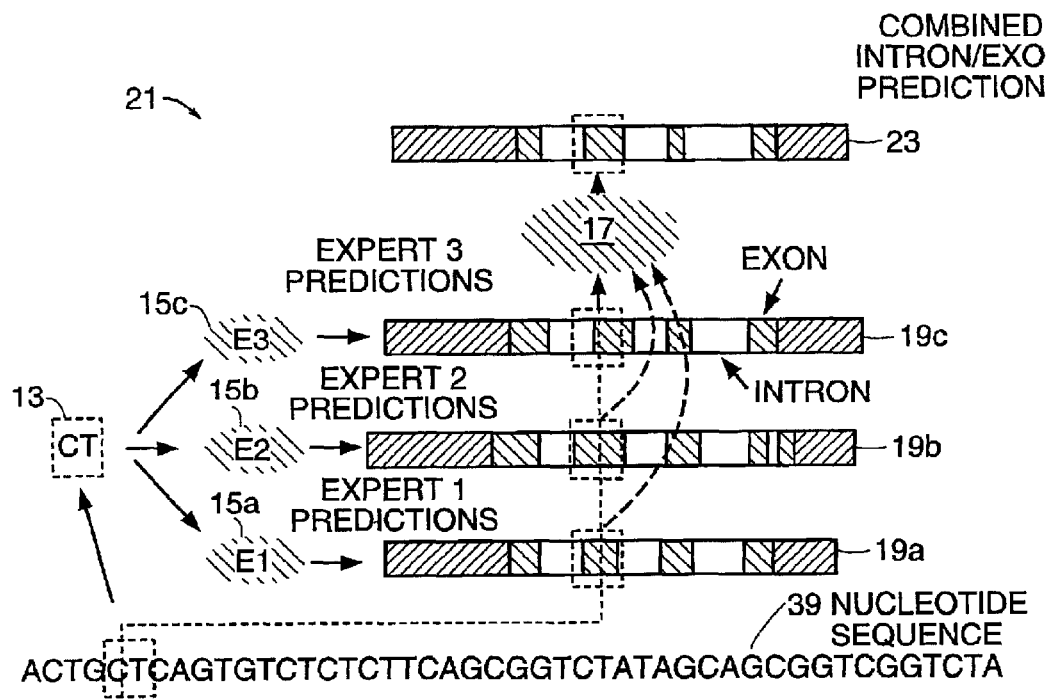

In particular, invention software 21 provides the input character string 13 corresponding to the subject nucleotide sequence 39, to plural expert systems 15a,b,c (FIG. 1B). The expert systems 15 are coupled in parallel to receive the input character string 13 and process the same. Example expert systems are Genie, Genmark, Genscan and Glimmer cited above. Each expert system 15 produces and outputs a respective intermediate exon/intron prediction 19 of the subject nucleotide sequence.

Output 19 of each expert system 15 is provided to previously trained Bayesian network combiner 17. Based on the results from training, Bayesian network combiner 17 combines the output (intermediate prediction of exons/introns) 19a,b,c of each expert system 15a,b,c accordingly. This results in a gene prediction/determination output by Bayesian network combiner 17 at 23.

Through appropriate I/O interface of digital processor 11, the invention software 21 supports display of the resulting gene prediction/determination 23. The display may be graphical indicia, textual indications, relative indications (relative to the input character string/subject nucleotide sequence) and the like.

Referring back to FIG. 1A, the Bayesian network combiner 17 is trained using known DNA sequences with known genes (exons/introns) as the training data 35. The training data is applied to the computer apparatus. That is, a corresponding character string representing the known DNA sequence is input to the invention software 21. Invention software 21 applies this training data character string to the expert systems 15. The expert systems 15 each determine/predict preliminary exons/introns 19 in the training data 35. The preliminary exon/intron predictions 19 from the expert systems 15 are fed into the Bayesian network combiner 17. In turn, the Bayesian network combiner 17 combines the preliminary exon/intron predictions 19 in a manner consistent with the known genes (exons/introns locations and pattern). That is, the Bayesian network combiner 17 is trained to make the combination of preliminary exon/intron predictions produce the known exons on output. In this way, the Bayesian network combiner 17 is said to be trained on the training data 35.

As a consequence of this training, a table or set of probabilities 37 of a given sub-sequence being a protein encoding gene (exon) results. This table 37 is employed during the processing of, i.e., applied to, test input character strings (subject nucleotide sequences) 13 discussed in FIGS. 1A and B above. In the preferred embodiment, the table 37 is structured as a probability equation (Equations 1–3 below) and the Bayesian network combiner 17 is structured as one of the corresponding models discussed next.

Figure 2:
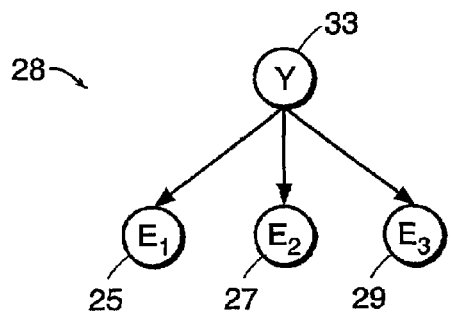
FIG. 2 illustrates a static naive-Bayes gene prediction combiner for the invention apparatus of FIG. 1.

Bayesian networks are probabilistic models that graphically encode probabilistic dependencies between random variables. The graphical structure of the model imposes qualitative dependence constraints. An example of a Bayesian network for combining gene predictions from three expert systems $E_1$, $E_2$, $E_3$ is shown in FIG. 2. For example, a directed arc between variables Y and $E_1$ denotes conditional dependency of $E_1$ on Y, as determined by the direction of the arc. In addition to this graphical representation, Bayesian networks include a quantitative measure of dependencies. For each variable and its parents this measure is defined using a conditional probability function or a table. In the example of FIG. 2, one of such measures is the probability $P(E_1|Y)$. Together, the graphical structure and the conditional probability functions/tables completely specify a Bayesian network probabilistic model. This model, in turn, specifies a particular factorization of the joint probability distribution function over the variables in the network. Hence, FIG. 2 defines $$P(Y,E_1,E_2,E_3)=P(Y)P(E_1|Y)P(E_2|Y)P(E_3|Y).$$

Bayesian network probabilistic models provide a flexible and powerful framework for statistical inference as well as learning of model parameters from data. The goal of inference is to find a distribution of a random variable in the network conditioned on evidence (known values) of other variables. Bayesian networks encompass efficient inference algorithms, such as Jensen's junction tree (Jensen, F. V., An Introduction to Bayesian Networks, Spring-Verlag, 1995) or Pearl's message passing (Pearl, J., Probabilistic reasoning in intelligent systems, Morgan Kaufmann, San Mateo, Calif. 1998). Inside a learning loop, such algorithms may be used to efficiently estimate optimal values of a model's parameters from data (for instance, see Jordan, M. I. ed., Learning In Graphical Models, Kluwer Academic Publishers, 1998). Furthermore, techniques exist that can optimally determine the topology of a Bayesian network together with its parameters directly from data.

As probabilistic models, Bayesian networks provide a convenient framework for the combination of predictions from expert systems. Weights and influences of individual expert systems may be optimally learned from data rather than being ad hoc or user-specified. Applicants designed four Bayesian network architectures of increasing complexity for the problem of combining gene predictions, namely:
1. Static naive Bayes gene expert combiner 28 (FIG. 2).
2. Static full Bayes gene expert combiner 31 (FIG. 3).
3. Output hidden Markov model gene expert combiner 40 (FIG. 4).
4. Input hidden Markov model gene expert combiner 51 (FIG. 5).

Static Naive Bayes

The simplest Bayesian network for combining multiple gene predictors is a naive Bayesian classifier. An example of a naive Bayes gene prediction combiner 28 is shown in FIG.

2. In this figure, three gene predictors are represented as nodes 25, 27, 29 ($E_1$, $E_2$, $E_3$) and the combined prediction 33 is denoted Y. Given the prediction of individual expert systems 25, 27, 29 ($E_1$, $E_2$, $E_3$), an optimal combined prediction 33 is found using the Bayesian inference $$Y^* = \max_Y P(E_1|Y) P(E_2|Y) P(E_3|Y) P(Y). \qquad \text{Equation 1}$$

Gene combiner parameters, probability tables $P(E_1|Y)$ and $P(Y)$, are learned from a training dataset of nucleotide sequences by statistically calculating $P(E_1|Y)$ and $P(Y)$ of all individual predictors $E_1$ and labeled for ground truth Y. For instance, a maximum likelihood (ML) estimate of these parameters for a training set of N nucleotides is $$P(E_i = e \mid Y = y) = \frac{\#E_i = e, Y = y}{N}$$

where e denotes the prediction of an expert system i, $e \in \{\text{intron, exon}\}$, and y is the combined prediction, $y \in \{\text{intron, exon}\}$. $\#\, E_1=e$, $Y=y$ denotes the number of cases in the training dataset where the prediction of expert system i is e and the ground truth is y. Alternative estimates of these parameters may be obtained using MAP (maximum a posteriori) estimation.

This modeling scheme 28 assumes independence of individual expert systems/nodes, given a known combined prediction. In the context of genome annotation, this would imply that the annotation of the expert systems 25, 27, 29 is independent given the true annotation. Although a successful technique in a wide range of machine learning tasks, the naive Bayes combiner 28 loses its charm as it neither models the correlation of individual expert systems nor the dependence between the adjacent nucleotides in the subject sequence.

Static Full Bayes

Correlation between individual expert systems may be modeled using a full Bayes model 31. This is shown in FIG. 3.

The optimal combined prediction 33 of predictions from the individual expert systems 25, 27, 29 ($E_1$, $E_2$, $E_3$) here is $$Y^* = \max_Y P(Y|E_1, E_2, E_3) \qquad \text{Equation 2}$$

Figure 3:
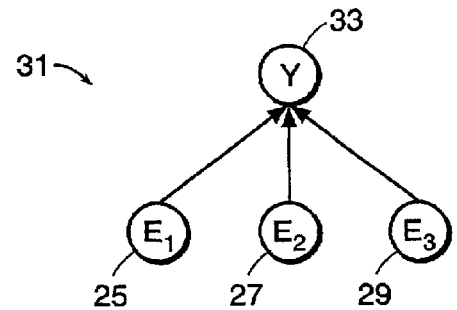
FIG. 3 illustrates a static full Bayes gene prediction combiner for the invention apparatus of FIG. 1.

Rather than a product of probabilities associated with individual expert systems, as is the case in the naive Bayes combiner 28 of FIG. 2, the full Bayes 31 in FIG. 3 associates one probability with each combination of those experts/nodes 25, 27, 29. The parameter of the full Bayes combiner 31, $P(Y|E_1, E_2, E_3)$, can again be learned from a training dataset, similar to the case of the static naive Bayes combiner 28.

It can be easily shown that the performance of the full Bayes model 31 is at least as good as that of the best individual expert system 25, 27, 29. Furthermore, the previously used AND, OR and majority models are special cases of the full Bayes combiner 31. Nevertheless, this model 31 still assumes that the annotation of a particular nucleotide is independent of the annotation of any other nucleotide in the sequence.

Output Hidden Markov Model

Hidden Markov model (HMM) is a Bayesian network that models probabilistic dependence between adjacent samples in a sequence. An HMM architecture 40 may also be used for combining outputs of individual gene predictors 25, 27, 29 as shown in FIG. 4.

Figure 4:
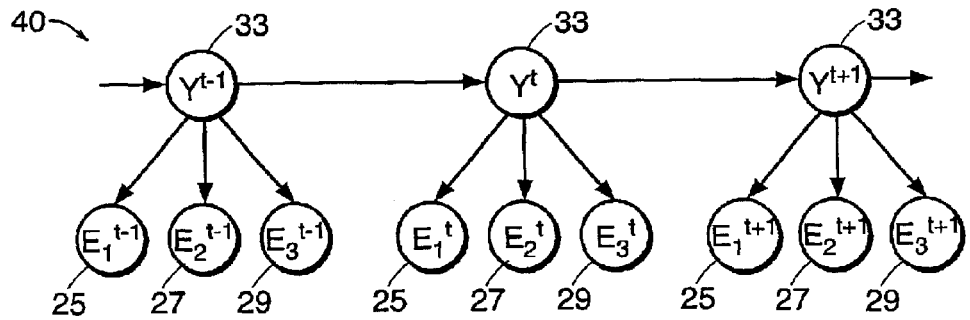
FIG. 4 illustrates an output hidden Markov model gene prediction combiner for the invention apparatus of FIG. 1.
Figure 5:
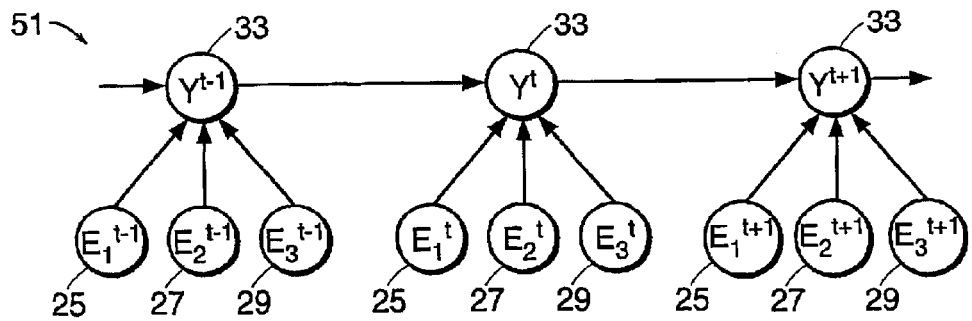
FIG. 5 illustrates an input hidden Markov model gene prediction combiner for the invention apparatus of FIG. 1.

Index t in FIG. 4 refers to the sample at location t in the subject nucleotide sequence. For instance, the sequence $Y^{t-1}, Y^t, Y^{t+1}$ gives the combined annotation for the subject nucleotide sequence n positions t−1, t, and t+1 respectively.

HMM model probabilistic dependence between the samples at adjacent positions, t and t−1. Namely, the output HMM combiner 40 proposed here is a sequential extension of the static naive Bayes model 28 of FIG. 2. Optimal gene prediction using this model 40 and given predictions of individual experts 25, 27, 29 may be obtained using classic inference/Viterbi decoding in HMMs.

Input Hidden Markov Model

The HMM-inspired architecture addresses the problem of sequential correlation of expert systems 25, 27, 29, however it does not model the correlation of individual expert systems at the same position in a sequence (much like the static naive Bayes 28). Applicants propose a modified network shown in FIG. 5 as the Bayesian network combiner 51 that combines the predictions of individual expert systems 25, 27, 29 while modeling all the interesting properties. This model 51 captures the dependencies between individual expert systems as well as the dependencies between adjacent nucleotides.

Probabilistic analysis for optimal prediction in the input HMM 51 is different from an ordinary HMM and the output HMM 40 discussed above. Nevertheless, a simple "forward-propagating" solution is defined and obtained as:

$$Y^*_t = \max_{Y_t} P(Y_t | E_1, E_2, E_3, Y^*_{t-1}) \qquad \text{Equation 3}$$

Indeed, the solution indicates the necessary sequential dependence of combining decisions.

Learning of input HMMs 51 is often not feasible in domains with large state spaces and sparse data points. However, the choice of the state space (as described in the section to follow) and abundance of data in genomic sequences make these models 51 appealing in this domain.

Experiments

The annotated drosophila sequence was used to conduct the experiments and to obtain the measure of the systems performance. The data is a 2.9 Mb long sequence of nucleotides. Applicants used three expert systems Fgenes CGGI (Salamov, A. A. and V. V. Solovyev, "Ab initio gene finding in drosophila genomic dna., *Genome Research*, Vol. 10, pp. 516–522, 2000); Genie EST (Reese, M. et al., "Genie—gene finding in drosophila melanogaster," *Genome Research*, Vol. 10, pp. 529–538, 2000); and HMM Gene (Krogh, A., "Using database matches with hmmgene for automated gene detection in drosophila, *Genome Research*, Vol. 10, pp. 523–528, 2000). Applicants' goal was to annotate the sequence into exon (coding region) and intron (non coding region) using a combination of expert systems.

For that purpose, Applicants assumed that each individual expert system provides the following binary decision. An expert system produces a single labeling for every nucleotide in a sequence: E if the nucleotide is a part of an exon and I if it belongs to an intron. Using the notation of Applicants' models, $E_i \in \{E, I\}$ for an expert i. Similarly, a combined decision Y is either E or I. Parameters of each of the four above-discussed models of Bayesian network combiners 28, 31, 40, 61 were learned using a standard maximum likelihood estimation in the Bayesian network framework. All prediction results were then obtained using a five-fold cross-validation.

To compare the performance of the combined system with that of the individual expert systems, Applicants used the following performance measures:

Sensitivity and Specificity

The results are presented at both the base level and the exon level. Sensitivity and specificity are the two measures that are used at the base level. These are defined as $$SN = \frac{TP}{TP + FN} \text{ and}$$

$$SP = \frac{TP}{TP + FP}$$

TP, FP, FN refer to True Positive, False Positive and False Negatives, respectively. Specifically, TP refers to those nucleotides that were correctly labeled as exons. FP refers to nucleotides that were labeled as exons even though they were actually part of introns. Finally FN are nucleotides that were labeled as introns while the actual annotation claimed them to be a part of exons.

Overpredicted and Missed Exons

Figure 6:
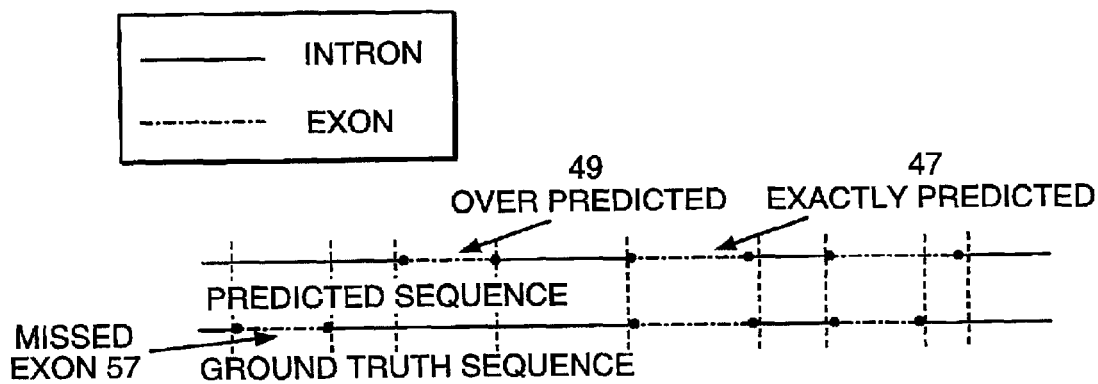
FIG. 6 illustrates exon level performance measure and terms.

Two more measures of error were used only at the exon level: overpredicted exons and missed exons. FIG. 6 provides some insight into the performance measures at the exon level.

An axon is said to be exactly predicted 47 only if both its ending and beginning points coincides with that of a true exon. An exon is said to be missed 57 if there is no overlap with any of the predicted exons. ME gives the percentage of missed exons 57 whereas WE gives the percentage of wrongly or overpredicted exons 49. To compute these two numbers (ME and WE), Applicants look for any overlap between a true and a predicted exon.

The performance results for the three expert systems (Fgenes CGG1, Genie EST and HMM Gene) along with that of "Genie" (mentioned previously) are presented in Table 4.1 and Table 4.2. Base level results are presented in Table 4.1 while Table 4.2 gives the performance of the experts at the exon level. Applicants also present an entry in the table (ME+WE) which gives some kind of measure of the overall performance of the expert systems at the exon level.

TABLE 4.1

Base level performance of some expert systems.

|    | Fgenes CGG1 | Genie | GenieEST | HMM Gene |
|----|-------------|-------|----------|----------|
| Sn | 0.89        | 0.96  | 0.97     | 0.97     |
| Sp | 0.77        | 0.92  | 0.91     | 0.91     |

TABLE 4.2

Exon level performance of some expert systems.

|         | Fgenes CGG1 | Genie | GenieEST | HMM Gene |
|---------|-------------|-------|----------|----------|
| Sn      | 0.65        | 0.70  | 0.77     | 0.68     |
| Sp      | 0.49        | 0.57  | 0.55     | 0.53     |
| ME      | 10.5        | 17.4  | 20.1     | 20.2     |
| WE      | 31.6        | 17.4  | 20.1     | 20.2     |
| ME + WE | 42.1        | 25.5  | 24.9     | 25.0     |

Table 4.3 and Table 4.4 show results for the mixture (combination) of expert systems framework. Applicants give results for the static Naive Bayes combiner 28 (SNB), Static full Bayes combiner 31 (SFB), Output HMM combiner 40 (OHMM) and Input HMM combiner 51 (IHMM). Applicants also provide benchmark performance measures for standard AND and OR combination of expert systems. Other than being two of the simplest combination techniques the AND and OR combiners also provide sensitivity and specificity bounds. The specificity for the AND case is 94% and this is the bound on what can be achieved using a (static) combiner of expert systems framework. Similarly the sensitivity of the OR sequence (98%) bounds the achievable sensitivity.

The base level results indicate that an improvement in prediction can be obtained by using the mixture (combiner) of expert systems framework. However, a look at exon level performance in Table 4.4 reveals a substantially more significant improvement. One sees that IHMM combiner 51 performs significantly better than any of the individual expert systems as well as better than any of the other expert system combination techniques. The overall performance (WE+ME) shows an improvement of 10% over the best individual expert system. One also observes that the sensitivity and specificity of the IHMM combiner 51 are better than that of all the individual expert systems. SNB's (combiner 28) poor performance stems from its incapability to model individual predictor correlations. Similarly, the OHMM combiner 40 showed poor base-level performance. However, its improved exon level performance indicates its ability to capture global sequential dependencies. Finally, the static full Bayes combiner 31 (SFB) performed very well at both the base and the exon levels. This reflects the model's 31 use of information contained in the correlation of the predictions of individual expert systems.

TABLE 4.3

Base level performance of mixture of expert systems framework.

|    | OR   | AND  | SNB  | SFB  | OHMM | IHMM |
|----|------|------|------|------|------|------|
| Sn | 0.98 | 0.86 | 0.97 | 0.97 | 0.93 | 0.97 |
| Sp | 0.74 | 0.94 | 0.84 | 0.92 | 0.79 | 0.92 |

TABLE 4.4

Exon level performance of mixture of expert systems framework.

|         | OR    | AND   | SNB   | SFB   | OHMM  | IHMM  |
|---------|-------|-------|-------|-------|-------|-------|
| Sn      | 0.73  | 0.55  | 0.75  | 0.78  | 0.49  | 0.77  |
| Sp      | 0.58  | 0.42  | 0.45  | 0.63  | 0.39  | 0.66  |
| WE      | 40.05 | 8.41  | 31.15 | 14.02 | 19.11 | 12.72 |
| ME      | 1.69  | 16.95 | 18.08 | 2.54  | 17.89 | 2.54  |
| WE + ME | 41.74 | 25.36 | 49.23 | 16.56 | 37.00 | 15.26 |

While this invention has been particularly shown and described with references to preferred embodiments thereof, it will be understood by those skilled in the art that various changes in form and details may be made therein without departing from the scope of the invention encompassed by the appended claims.

For example, where the term nucleotide sequence or genomic sequence is used, it is understood that a DNA or RNA sequence or fragment thereof, or the like applies.

Further, a variation or hybrid of Bayesian network combiners may be used. This may be accomplished by a multiplexing among the different Bayesian network models 28, 31, 40, 51 as a function of the input genomic sequence fragment from a whole subject sequence.

It is understood that other means for preliminarily predicting genes (gene location) may be used instead of the expert systems. Other gene predictors may be employed along with or in place of the expert systems.

What is claimed is:

1. A method for automated gene prediction, comprising the steps of:
    obtaining from a plurality of expert systems a plurality of respective preliminary gene location predictions for a subject gene in a subject genomic sequence;
    inputting into a digital processor programmed to contain a Bayesian network a plurality of respective datasets representing said gene location predictions;

combining said respective datasets in said Bayesian network; and forming from said Bayesian network a data output indicating an improved predicted location for said subject gene in the subject genomic sequence, wherein the Bayesian network includes probabilistic dependencies between individual expert systems and dependencies between adjacent parts of the subject genomic sequence.

2. The method as claimed in claim 1 wherein said Bayesian network combines said plurality of datasets according to the probability equation $$Y^* = \max_{Y_t} P(Y_t | E_1, \ldots, E_n, Y^*_{t-1})$$

$$E_i \in \{E, I\}$$

wherein t is location of a subject gene in the subject genomic sequence and $E_1, \ldots, E_n$ are the respective predictions (E for exon or I for intron) made by individual expert systems, n being the number of expert systems in the plurality.

3. The method as claimed in claim 1 wherein the subject genomic sequence is a DNA or RNA sequence.

4. The method as claimed in claim 1 wherein said obtaining and said inputting each comprise predicting an exon location.

5. A method as claimed in claim 4 wherein gene locations further include exon and intron predictions; and the final combined output indicates exons and introns of the predicted genes of the subject genomic sequence.

6. The method of claim 1 wherein said forming comprises creating from said Bayesian network a data output indicating an optimal combined predicted location for each said subject gene in the subject genomic sequence.

7. The method of claim 1 comprising, prior to said combining, providing a training dataset to said processor representing a plurality of known gene locations on a known genomic sequence.

8. The method of claim 7 comprising, constructing a conditional probability function or table from said training dataset.

9. The method of claim 1 comprising selecting a subject gene that is unknown to said expert systems.

* * * * *